United States Patent [19]
Welker

[11] Patent Number: 4,942,772
[45] Date of Patent: Jul. 24, 1990

[54] STACK SAMPLING SYSTEM

[75] Inventor: Thomas F. Welker, Sugar Land, Tex.

[73] Assignee: Welker Engineering Company, Sugar Land, Tex.

[21] Appl. No.: 368,418

[22] Filed: Jun. 19, 1989

[51] Int. Cl.$^5$ .............................................. G01N 1/24
[52] U.S. Cl. .................................................. 73/863.83
[58] Field of Search ........................ 73/863.81–863.86, 73/864.34, 864.62, 864.63

[56] References Cited
U.S. PATENT DOCUMENTS

| | | | |
|---|---|---|---|
| 2,814,952 | 12/1957 | Ryant, Jr. et al. | 73/863.83 |
| 3,793,888 | 2/1974 | Rosenwald | 73/864.62 |
| 3,885,437 | 5/1975 | Reagan | 73/863.82 |
| 3,960,500 | 6/1976 | Ross et al. | 73/863.81 |
| 4,037,475 | 7/1977 | Topham | 73/863.83 |
| 4,094,187 | 6/1978 | Navarre, Jr. | 73/864.34 |
| 4,134,289 | 1/1979 | Bohl et al. | 73/864.34 |
| 4,317,379 | 3/1982 | Oberlander et al. | 73/863.83 |

FOREIGN PATENT DOCUMENTS

| | | | |
|---|---|---|---|
| 2343239 | 9/1977 | France | 73/863.83 |
| 2388268 | 12/1978 | France | 73/863.81 |
| 0092328 | 5/1984 | Japan | 73/863.83 |

Primary Examiner—Robert Raevis
Attorney, Agent, or Firm—Gunn, Lee & Miller

[57] ABSTRACT

The present disclosure is directed to a controlled, timed, cyclically operated sample taking apparatus for use with a stack. A fitting at the top portion of the stack positions a probe having an opening for removal of a gas sample from the stack discharge stream which sample is delivered along a sample line on the stack to ground located equipment. The sample stream is delivered through a means which periodically is operated to take a portion of that sample and deliver that through a sample storage line into a constant pressure storage cylinder. The cylinder is filled to capacity. Surplus sample which is not required is returned through a aspirator powered by a flow of compressed air to boost the surplus or unwanted sample through a sample return line back into the stack discharge stream.

12 Claims, 3 Drawing Sheets

STACK SAMPLING SYSTEM

BACKGROUND OF THE DISCLOSURE

This disclosure is directed to a system for sampling gas discharges from a vent, blow down, flare or smoke stack. While smoke, vent, blow down or flare stacks can be small, they typically discharge large quantities of gases to atmosphere. Large sized stacks can easily discharge several thousand tons of effluent gases per day. The chemical content of the discharge gives rise to air pollution problems, including acid rain. A smoke, vent, blow down or flare stack discharge is normally resultant of a furnace, smelter operation or gas operation in which fossil fuels are converted into combustion produces discharged through the stack. In an ideal combustion situation, the fossil fuel materials are converted into $H_2O$ and $CO_2$ to thereby provide a discharge which is substantially clear and free of undesirable chemical products. In a smelter operation, ores may be processed with exposure to heat and might possibly discharge other gaseous products including $SO_x$, $CO$, and other partially or totally oxidized elements. One gas example is $NO_x$. The quantities of gas discharges become important from the point of view of controlling and limiting certain discharges. For instance, enhanced after-burning can be incorporated to reduce $CO$ discharge. Scrubbing can be incorporated to reduce particulate matter in the stack gas. Any number of additional discharge improvements can be implemented but they are generally not implemented unless one has a dynamic sample derived from the discharge.

It is not uncommon to connect a stack directly from a furnace or smelting operation so that the gases from the combustion chamber are discharged directly into the stack. In fact, the gases entering the stack may be at substantially elevated temperatures. The stack is normally constructed of firebrick and a similarly fire resistant lining is included at the lower portions of the stack. In fact, the fire brick and lining may extend practically the full length of the stack. A stack tends to draw dependent on scale factors including stack height. Velocities may be negligible in the lower portions of the stack and especially near the furnace. By contrast, the discharge gases travel quite rapidly as a result of buoyant forces as they approach the top of the stack. The hot gas discharge is lighter than the ambient atmosphere as a result of heating. This stream of hot gases typically accelerates as it approaches the top end of the stack. Many stacks are built as tall as 600 feet so that the discharge is substantially cooled and is much more homogenous in nature at the top of the stack. Afterburning to the extent that it might occur in the firebox or furnace discharge and while rising in the stack, is substantially complete so that the gases discharged to atmosphere can be captured best only at the top portions of the stack. Accordingly, the stream of discharge gases from the stack is best sampled at the top of the stack.

It is possible to derive a sample from lower regions of the stack, but it is questionable whether or not such a sample will represent the actual discharge to atmosphere. For that reason, the stack discharge is best sampled at the top of the stack. Moreover, entry into the stack interior is more readily accomplished at the top where the discharge is cooler, after-burning has substantially been completed, and the stream is more thoroughly mixed. For flare, vent or blow down stacks the gas product flowing to the top of the stack moves through a line when a valve is opened to vent gases through a flare into the atmosphere. To confirm to the governing agencies that the gases vented are not banned, the present apparatus is a system best installed near the top of the stack for collecting a sample. The system incorporates a protruding probe having an opening at the end thereof which is positioned approximately along the stack's center line near the top end to take a sample of the discharge from the stack. The sample is quite small compared to the volume of gases flowing through the stack. Stacks presently exist which discharge over 1,000 tons of hot gases daily; while such a flow rate is extraordinarily large, the sample is extraordinarily small compared with the total flow. The sample is much smaller than one part in a hundred, indeed, is about one part in $10^6$ or $10^8$. Even then, that sample which is delivered to the apparatus of the present disclosure may be quite large and must be reduced in size again as will be discussed.

The present disclosure is directed to a sample system which incorporates an inlet installed in a stack for obtaining a sample. This sample is delivered along a small line on the stack to the sample measuring apparatus of the present disclosure. The large sample is further metered through a system which reduces the size of the sample or specimen even further. This step again reduces the size of the sample in contrast with the stack discharge by another two, three or four orders of magnitude so that the sample size to the stack discharge can be controllably scaled to be as large as one part per $10^5$ down to one part in $10^{10}$. Indeed, even smaller samples can be taken as desired by serially connecting additional sample removing means.

It is important that a sample be truly representative. To this end, the present apparatus sets forth a timed sampling system which operates periodically, preferably in proportion to the flow through the stack and perhaps once per hour, once per minute, once per ten seconds, etc. Samples taken at a controlled time rate are delivered into a storage container so that the storage container cumulatively stores a continuous sample flow preparatory to testing by the operator. This stored sample is thus proportionate to the discharge of the stack for the collection time interval. Assume that the collected samples are derived from a ten day period. In that instance, the storage container is provided with the intended proportionate specimen collected over ten days. The sample collected in ten days thus should provide a precise analysis of the stack discharge over the ten day interval. It can be taken conveniently to a laboratory for testing for constituents including $SO$, $SO_x$, $NO$, $NO_x$, $CO$, and any other discharge from the stack.

The present apparatus thus takes advantage of the height of a stack. The sample is more like the actual atmospheric discharge at the top end of the stack. Moreover, the afterburning which might be involved in the lower portions of the stack is substantially complete by the time the discharge gases reach the top of the stack. Another benefit is that mixing and commingling occurs so that the sample is more true to the effluent flow in the stack. Last of all, it is not necessary to attempt to enter the stack at the lower regions typically made of materials which are difficult to penetrate, namely an inside liner and firebrick. The liner is normally formed of ceramic materials which are difficult to work with. This device permits the installation of equipment operative at lower temperatures.

The apparatus of this disclosure is a system which can be installed with an intake at or near the top of a smoke stack, and which incorporates a sample line extending down the stack to equipment located at or near the ground at the base of the smoke stack. Equipment includes a constant pressure storage cylinder which has an internal piston which moves to provide a chamber for storage of the sample. The equipment also includes apparatus which proportions the sample and delivers it at a controlled rate for storage. The timing may be interfaced with measurement to provide a sample taken proportional to the flow in the line or out the stack. A timer operates a solenoid valve which periodically is switched off and on to provide timed operation to a diaphragm powered plug cutting apparatus which cuts a plug from the sample flow from the stack. In addition, there is an aspirator which is driven by a supply of compressed air for the purpose of forcing surplus sample into a stack return line which is extended along the stack and which empties at the common fitting supporting the inlet at the top of the stack.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
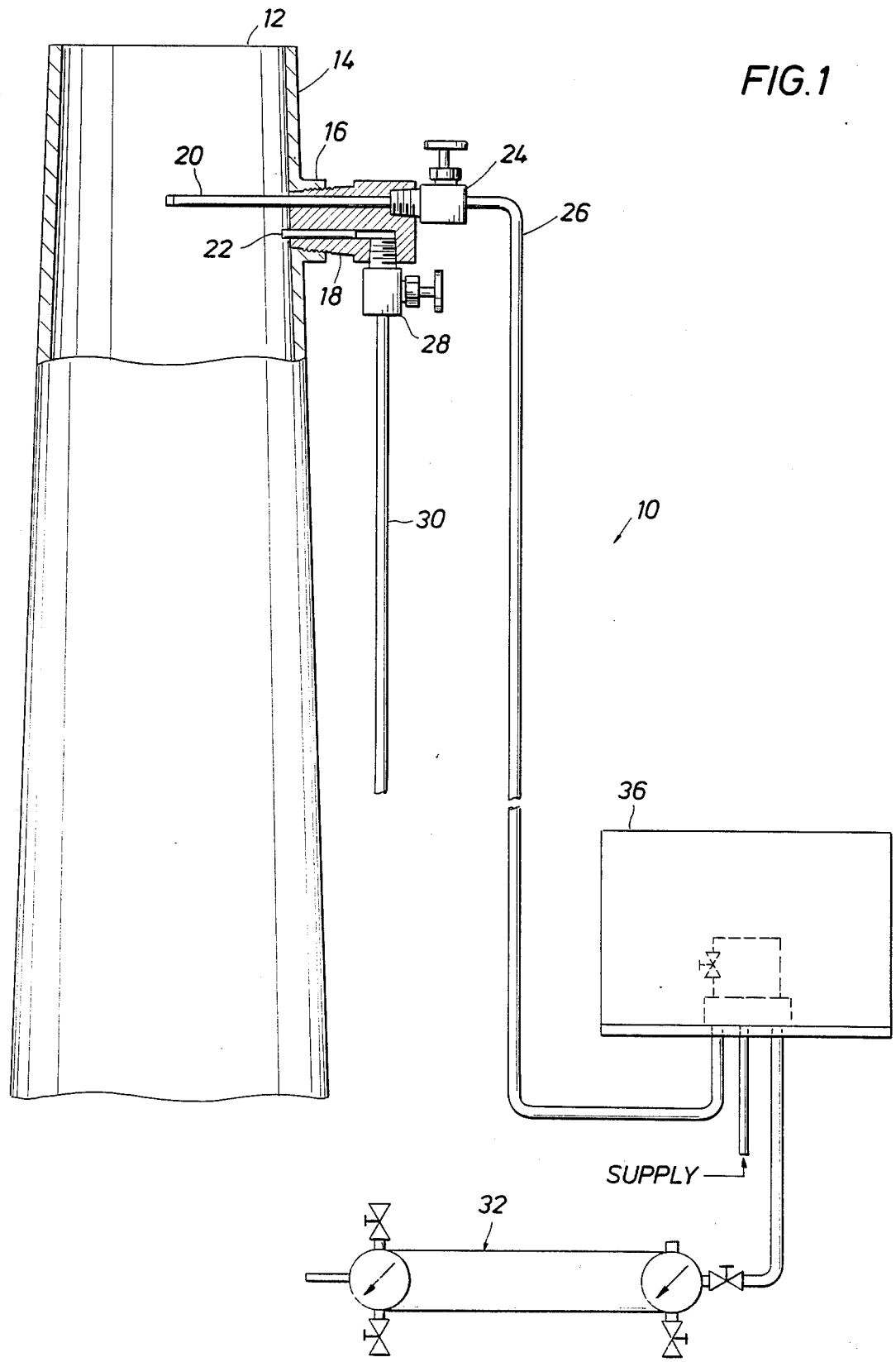
FIG. 1 shows a stack sampling apparatus installed at the top of the stack and includes a sample line extending along the stack to an apparatus located at or near the lower portions of the stack for collecting the sample in a constant pressure storage vessel.

Attention is first directed to FIG. 1 of the drawings where the present sampling apparatus is identified by the numeral 10. It is installed at or near the top of a stack 12. The stack is open at the upper end. It is formed of a tapered wall 14 which supports a collar 16 which is internally threaded to receive a threaded plug body 18. The body 18 is drilled with multiple passages. This enables two flow paths to be established through the body 18. The stack 14 is preferably made of metal at the top portions but it is typically lined with firebrick and a ceramic coating at the lower portions. The protective materials can be extended up the stack to a height determined by the temperature exposure arising during operation of the stack.

The numeral 20 identifies a sampling probe which has an open tip for drawing sample from the stack. The numeral 22 identifies a shorter probe which opens into the stack for returning surplus sample as will be described. A sample is thus taken without interference from the returned surplus sample.

The body 18 supports two external valves, one being identified at 24. It is a cut-off valve which is normally left open to provide flow through the sample line 26. In addition, a normally open valve 28 is also included. The surplus sample return line 30 connects to the valve 28 and returns surplus sample.

FIG. 1 shows certain portions of the equipment which are located at the nearby ground location approximately at the base of the stack. This equipment can be immediately at the base of the smoke stack or within shelter of a building nearby. In any event, the equipment includes a constant backpressure storage cylinder 32 as will be described. In addition to that, the numeral 36 identifies a closed cabinet or housing which encloses the control equipment for operation of the sampling apparatus 10.

Figure 2:
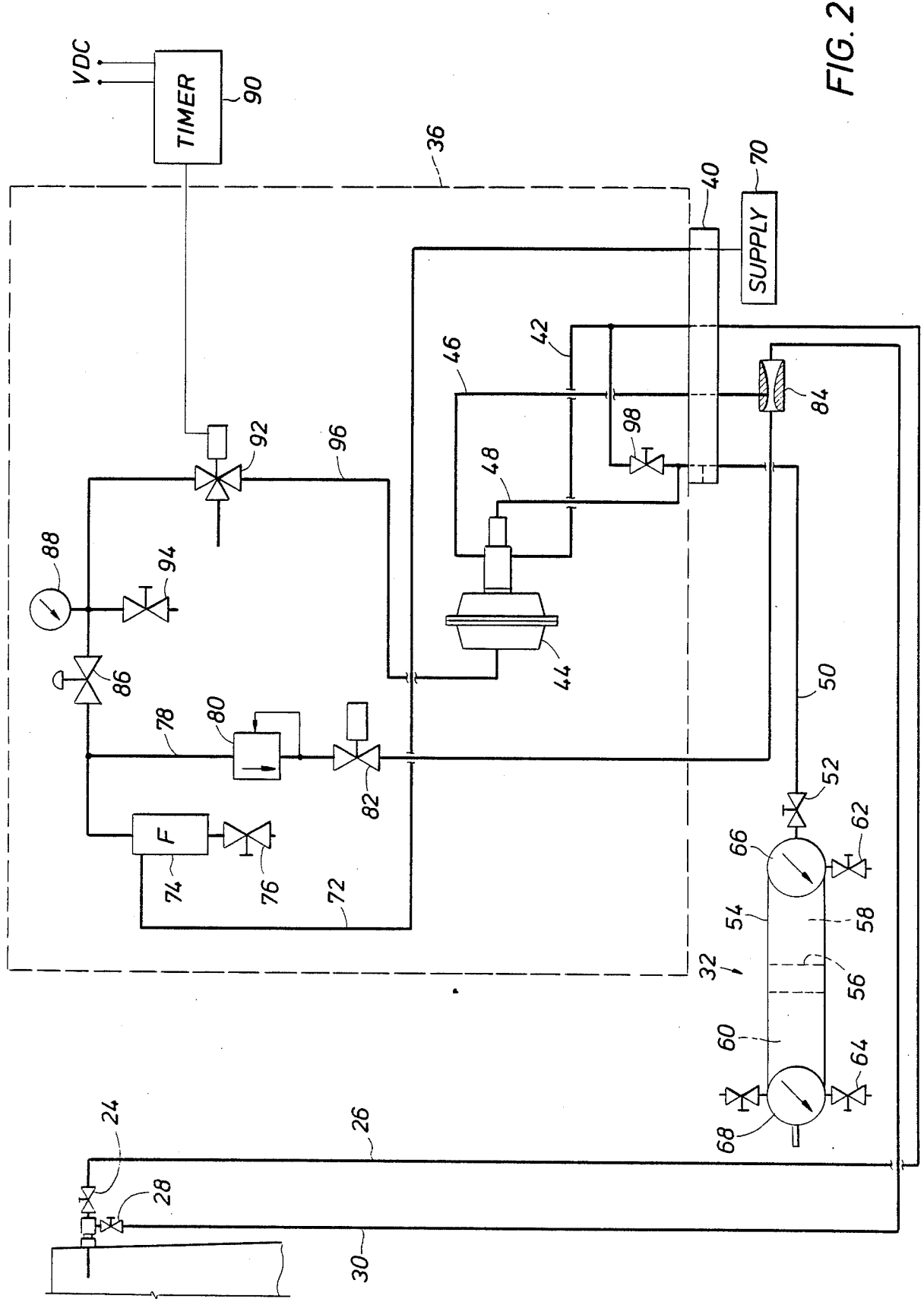
FIG. 2 is a schematic of the equipment which obtains the sample, proportions the sample to derive a portion for storage and which returns surplus sample back to the stack.

Attention is now directed to FIG. 2 of the drawings which illustrates the sample line 26 and the surplus line 30. They are typically parallel to one another, supported on the side of the stack and extend from the top of the stack and connect with the circuitry which is shown in FIG. 2 of the drawings. The cabinet or housing 36 is shown in dotted line and encloses the equipment which is shown in FIG. 2 within the dotted line. The housing supports an interface 40 which has a number of lines into and out of the housing. One of the lines is the sample feed line 42 which is input to a diaphragm powered apparatus 44. Its function will be made more clear hereinafter. All the sample which flows in through the line 42 and not removed by the apparatus 44, flows out through the waste line 46. Only a small portion is removed by the apparatus 44, and that portion is delivered through the sample line 48.

The diaphragm powered apparatus 44 is described in U.S. Pat. No. 3,945,770 and functions to remove a portion of the flow from the line 42. That portion is delivered into the line 48. The portion which is actually taken is quite small, typically representing one part per thousand or perhaps even one part per hundred thousand of the flow. This depends in part on the frequency at which the apparatus 44 is operated. Since it serves as a proportioning device, it will be denoted as that type equipment hereinafter. In other words, it takes the larger sample flow from the sample line 26, and periodically operates to remove a sample of specified size. That sample is delivered to the line 48 and then into the line 50 through the manifold 40. The line 50 is normally opened by a valve 52 serving as an input valve for the storage cylinder 32.

The storage cylinder 32 incorporates an elongate cylinder 54 which is internally axially hollow and which is closed across the middle by means of a piston 56 shown in dotted line. This defines a chamber to be filled 58, and there is a second chamber 60 on the other side of the piston which is emptied as pressure fluid is introduced. The chamber 60 holds backpressure. A valve 62 is used to empty the chamber 58 after it has been filled. The chamber 60 is drained through a regulator valve 64. Pressure in the upstream chamber 58 is indicated by a pressure gauge 66 while the second chamber pressure is measured by a pressure gauge 68. This apparatus is initially installed with a valve 52 closed, the chamber 58 evacuated, the piston 56 at the right, and the chamber 60 filled with pressure fluid to a specified pressure level. As flow is introduced through the valve 52, a constant backpressure is maintained. The mode of operation of the proportioning apparatus 44 controllably delivers equal bite sized portions from the sample flow so that the samples taken thereby are ratably delivered and forced into the storage cylinder 32 at the back-pressure maintained in the system. This assures filling of the storage cylinder 32 so that the sample can be removed to a laboratory for testing for various constituents.

FIG. 2 of the drawing indicates a source of compressed air at 70. The compressed air supply is delivered to a supply line 72 and is input through a filter 74. The filter is selectively drained by a drain valve 76. The filtered air supply provides two output lines. One is in the line 78. This flow is directed to a pressure regulator 80 and a solenoid valve 82 so that a regulated supply, switched on or off as required, is delivered through an aspirator 84. One function of this device will be described in detail below. It is powered however by the regulated pressure delivered from the line 78 and is typically in the range of about 40 to 80 psi.

Another output line is through a valve 86. This flow is introduced through several components into the line 96. Pressure in the line 96 is indicated by the pressure gauge 88. This flow is directed through a solenoid control valve 92. The line is vented to atmosphere by a valve 94. A similar vent or purge valve 98 is shown elsewhere. The solenoid valve 92 is switched on by a timer 90. The timer switches the solenoid valve periodically on and off. The sequence can be scaled to any ratio. For instance, one sample can be taken once per minute, once per hour, etc. The timer 90 determines this. When the solenoid valve is open, operating pressure is applied to the diaphragm motor at 44 so that a sample bite is taken.

Figure 3:
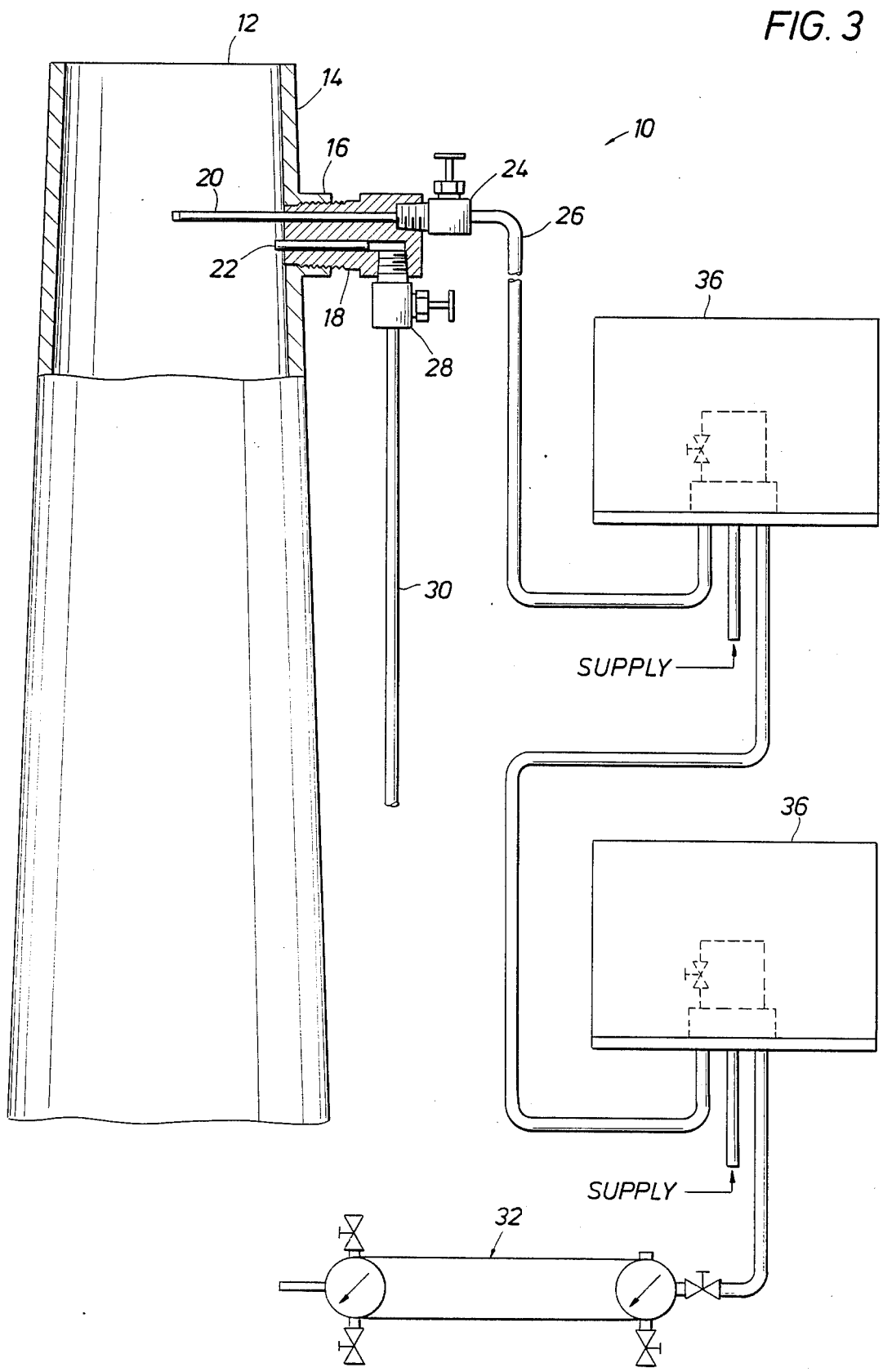
FIG. 3 shows a stack sampling system including two serially connected sample removing means.

FIG. 3 shows two serially connected sample removing means. Two or more sample means can be serially connected in this manner to further reduce the sample size removed and stored in the storage cylinder.

OPERATION OF THE SAMPLING SYSTEM:

Operation of the system will now be described so that the various components in FIG. 2 will be understood and the mode of cooperation made clear.

Assume that the valves 24 and 28 are left normally open so that the sample line 26 is able to collect sample and deliver it from the top of the stack to the equipment located in the cabinet 36. The flow through the line 26 is delivered through the interface 40 into the sample line 42 and surplus sample is delivered out of the apparatus through the line 46. The diaphragm powered apparatus at 44 is operated periodically to intercept a portion of the sample flowing from the line 42 into the line 48. It operates to remove a bite or plug from the flow. This scales down the size of the sample actually collected. This smaller sample portion is delivered out through the line 48, through the interface 40 and into the line 50, the valve 52 and the chamber 58 of the storage cylinder 32. It is collected, samples being removed periodically, all samples being delivered into the chamber 58, and the samples being accumulated until the removable cylinder is full.

Cylinder replacement is accomplished readily. The valve 52 is momentarily closed. This permits the detachable and removable cylinder to be taken from the installation and carried to a laboratory for testing. A substitute cylinder is installed. When it is installed, the chamber 58 is substantially evacuated, the piston 56 is at the right extremity of movement, a fixed backpressure is establish in the chamber 60 by the use of a regulator valve. Pressure in the chamber 60 is regulated by said regulator valve so that the piston 56 moves to the left as additional sample is delivered into the chamber 56. That is accomplished by connecting substitute storage cylinder through the valve 52, opening the valve into the chamber 58 and filling the chamber 58 with sample as obtained. Typically, the sample will accumulate in the cylinder for a long time interval, the interval being determined by various scale factors including the rate at which sample is collected and the size of the sample storage cylinder 32.

The apparatus 44 delivers sample through the line 48 against any prevailing backpressure. It is equipped with check valves so that flow assuredly is delivered for storage even though the backpressure may vary. It is desirable however to maintain the backpressure at a stabilized level, and to this end, that is accomplished by the constant pressure cylinder 32.

The sampling apparatus 44 operates periodically under control of the timer. It is provided with pressure for operation to collect a small bite or plug from the sample flow which is delivered into the line 48. The sampling rate can be controlled by control of the timer 90. Surplus sample is delivered out through the aspirator 84. It is delivered through the line 46 into a partial vacuum as a result of aspirator operation. The aspirator 84 is furnished with a regulated supply of air. The supply 70 delivers air through a line 72, the filter 74, the regulator 80 and the control valve 82. The flow is kept on at a regulated pressure perhaps 40–80 psi. This regulated flow is introduced to the aspirator 84 which draws a vacuum, the vacuum assuring that the surplus sample from the line 46 is pulled away from the equipment and into the aspirator. Since the air introduced into the aspirator is maintained at a modest pressure, this assures that the surplus sample is delivered through the return line 30, back up the stack through the valve 28 and into the stack discharge. This discharge line is useful in removing and disposing of surplus sample. This portion of the equipment operates continuously. This assures continuous disposal of the surplus sample.

While the foregoing is directed to the preferred embodiment of the present invention, other and further embodiments of the invention may be devised without departing from the basic scope thereof, and the scope thereof is determined by the claims which follow.

What is claimed is:

1. A system for obtaining a proportioned sample from a stack discharge gas flow, the system comprising:
   (a) an elongate stack sample line extending along a stack to upper portions thereof and connecting to a probe positioned in the upper portions of the stack and having an inlet opening, said probe receiving thereinto a sample of the stack discharge gas flow, and wherein said line delivers the sample to the base area of the stack;
   (b) cyclically operated sample removing means for periodically and repetitively removing a portion of the sample from said stack line wherein the removed portion is delivered through a sample outlet line;
   (c) storage means connected with said sample outlet line, said storage means comprising a chamber for receiving and holding gases therein to fill said storage means to a specified volume and including valve means for isolating the same therein to permit removal thereof for transfer to another location; and (d) means for timing operation of said sample removing means, said means incorporating a controllable timer and further including a timer controlled valve means for periodic operation of said sample removing means.

2. The system of claim 1 wherein said stack line extends to an interface at the base area.

3. The system of claim 1 wherein said removing means connects to a surplus sample return line connected to the stack for surplus sample disposal.

4. The system of claim 1 wherein said timing means comprises:
 (a) said timer;
 (b) said valve means connected to said timer for periodic operation;
 (c) a source of pressure fluid connected to said valve means for timed switching thereby; and
 (d) pressure fluid responsive means connected to said valve means for operation thereby for periodically delivering portions of the sample from said stack line for said storage means.

5. The system of claim 4 including a pressure regulator connected between said pressure fluid source and said valve means.

6. The system of claim 4 including aspirator powered means directing surplus sample from said sample removing means.

7. The system of claim 1 wherein said sample line extends from a fitting installed in the upper portions of said stack, and extends along said stack to the base thereof, thereby delivering sample in excess of that which is required, and further including a surplus sample return line extending along said stack to the point at which said sample line connects with said stack for returning excess surplus sample into said stack, and further including means for providing a positive pressure drive to said sample return line.

8. The system of claim 7 wherein said means providing positive pressure drive includes a supply of compressed air delivered into said sample return line and said sample return line incorporates a serially connected aspirator forming a pressure differential assisting return of surplus sample into said sample return line.

9. The system of claim 8 wherein said positive drive means comprises said aspirator having a vacuum port connected to said surplus sample return line to pull surplus sample for stack return.

10. The system of claim 1 including a second sample removing means connected serially to said sample removing means for additional sample size reduction.

11. The system of claim 10 wherein said second sample removing means is serially connected to the output of said sample removing means.

12. The system of claim 1 including an enclosure for said sample removing means.

* * * * *